United States Patent [19]

Schloemer

[11] Patent Number: 4,654,438

[45] Date of Patent: Mar. 31, 1987

[54] MANUFACTURE OF ALPHA-ARYLALKANOIC ACIDS AND PRECURSORS

[75] Inventor: George C. Schloemer, Lyons, Colo.

[73] Assignee: Syntex Pharmaceuticals International Limited, Hamilton, Bermuda

[21] Appl. No.: 741,655

[22] Filed: Jun. 5, 1985

Related U.S. Application Data

[60] Division of Ser. No. 502,036, Jun. 7, 1983, which is a continuation of Ser. No. 259,119, Apr. 30, 1981, abandoned.

[51] Int. Cl.$^4$ .................... C07C 69/76; C07C 53/134
[52] U.S. Cl. ................................ 562/496; 568/591; 560/56; 562/466; 562/490; 260/456 R
[58] Field of Search .................. 562/496, 466, 490; 560/56; 558/51; 568/591

[56] References Cited

U.S. PATENT DOCUMENTS 4,539,420  9/1985  Tsuchihashi et al. ............... 560/105

*Primary Examiner*—Paul J. Killos
*Attorney, Agent, or Firm*—John A. Dhuey; Joseph I. Hirsh

[57] ABSTRACT

α-Arylalkanoic acids or esters, orthoesters or amides thereof are prepared by forming an α-hydroxy ketal or thioketal of an aryl alkyl ketone, activating the α-hydroxy substituent with an esterifying agent to form the corresponding ketal or thioketal ester substrate, wherein the ester group is sufficiently labile to non-catalytically disassociate from the substrate in a protic or dipolar, aprotic solvent, maintaining the ester substrate in contact with the protic or dipolar, aprotic solvent or mixtures thereof for a time sufficient to form the corresponding α-arylakanoic acid or ester, orthoester or amide thereof, and optionally concomitantly or sequentially hydrolyzing any ester, orthoester or amide formed to the corresponding α-arylalkanoic acid.

21 Claims, No Drawings

MANUFACTURE OF ALPHA-ARYLALKANOIC ACIDS AND PRECURSORS

This is a division of application Ser. No. 502,036 filed June 7, 1983 which is a continuation of application Ser. No. 259,119 filed Apr. 30, 1981 now abandoned.

BACKGROUND OF THE INVENTION

Field of the Invention

The present invention relates to processes and novel intermediates utilized therein for preparing pharmaceutically useful α-arylalkanoic acids. In particular, the present invention utilizes novel α-hydroxy alkyl aryl ketals activated with a labile ester leaving group, which are solvolytically and non-catalytically rearranged to the corresponding α-arylalkanoic acids or esters, orthoesters or amides thereof. Optional concomitant or sequential hydrolysis of any ester, orthoester or amide formed yields the corresponding and desired α-arylalkanoic acids.

State of the Art

Numerous α-arylalkanoic acids (i.e. 2-arylalkanoic acids) have been described and developed and found to be useful as pharmaceutical agents exhibiting anti-inflammatory, analgesic and anti-pyretic activity. For example, U.S. Pat. No. 3,385,386, describes certain 2-phenylpropionic acids useful for their anti-inflammatory activity. Particularly noteworthy of the compounds described therein is 2-(4-isobutylphenyl)propionic acid, known generically as ibuprofen. U.S. Pat. No. 3,600,437 describes 2-(3-phenoxyphenyl)- and 2-(3-phenylthiophenyl)alkanoic acids among other related compounds. Particularly noteworthy therein is the compound 2-(3-phenoxyphenyl)propionic acid, which is known generically as fenoprofen. U.S. Pat. No. 3,624,142 describes (fluoro-substituted biphenyl)alkanoic acids, among which is 2-(4'-fluoro-4-biphenyl)-propionic acid. U.S. Pat. No. 3,755,427 describes additional fluoro-substituted biphenylpropionic acids, among which is 2-(2-fluoro-4-biphenyl)propionic acid, known as flurbiprofen. U.S. Pat. No. 3,904,682 describes the compound 2-(6-methoxy-2-naphthyl)-propionic acid, which is known generically as naproxen and is a potent anti-inflammatory compound. Related compounds are described in Belgian Patent No. 747,812. U.S. Pat. No. 3,912,748 describes 5 and 6-benzoxyazoylalkanoic acids possessing anti-inflammatory, anti-pyrretic and analgesic activity. Notable among those compounds is 2-(4-chlorophenyl-5-benzoxazoyl)-propionic acid, known generically as benoxaprofen. Thus, it can be seen that a tremendous variety of useful α-arylalkanoic acids are known.

Other known, useful α-arylalkanoic acids are exemplified by 6-chloro-α-methyl-9H-carbazole-2-acetic acid (carprofen), α-methyl-9H-fluorene-2-acetic acid (cicloprofen), 3-chloro-o-methyl-4-(2-thienylcarbonyl)-benzene acetic acid (cliprofen), α-methyl-3-phenyl-7-benzofuranacetic acid (furaprofen), 4-(1,3-dihydro-1-oxo-2H-isoindol-2-yl)benzene acetic acid (indoprofen), 3-benzoyl-α-methylbenzene acetic acid (ketoprofen), 3-chloro-4-(2,5-dihydro-1H-pyrrol-1-yl)benzeneacetic acid (pirprofen), α-methyl-4-(2-thienylcarbonyl)benzeneacetic acid (suprofen) and compounds related thereto.

Numerous processes for the manufacture of such α-arylalkanoic acids have also been described. Such processes have been described in the aforementioned patents and in other patents and in the non-patent literature as well. For example, U.S. Pat. No. 4,135,051 describes a process route for preparing the ester precursors of many of the useful arylalkanoic acids utilizing trivalent thallium salts as reactants. Such a process suffers from the disadvantage that the thallium salts employed are toxic chemicals which must be removed from the final product. U.S. Pat. No. 3,975,431 describes the preparation of α-arylalkanoic acids from glycidonitriles through enol acylates. U.S. Pat. Nos. 3,658,863; 3,663,584, 3,658,858; 3,694,476; and 3,959,364 describe various coupling methods for preparing arylalkanoic acids. More recently, U.K. Patent publication No. 2,042,543 published Sept. 24, 1980, (corresponding to application Ser. No. 8005752, filed Feb. 20, 1980) describes a process for preparing the ester precursor of arylalkanoic acids from α-haloalkyl aryl ketones using a metal catalyst for catalytically inducing rearrangement in an acidic, alcoholic medium, the catalyst being silver (I) salts of organic and/or inorganic anions. The high costs associated with utilizing metal catalysts, particularly silver, in a large scale process is an inherent disadvantage to such a process. Accordingly, there remains a need for a simple, economical process for producing α-arylalkanoic acids of the types described.

SUMMARY OF THE INVENTION

In the process of the present invention, a non-catalytic rearrangement of a ketal or thioketal of an α-hydroxy alkyl aryl ketone is effected by activating the α-hydroxy moiety with an esterifying agent to form the corresponding alkyl aryl ketal or thioketal ester substrate. The ester group is chosen to be sufficiently labile to disassociate from the substrate upon contact with a protic or dipolar, aprotic solvent medium. The ester substrate is maintained in contact with the protic or dipolar, aprotic solvent or a mixture thereof for a time sufficient to form the α-arylalkanoic acid or ester, orthoester or amide thereof, and optional concomitant or sequential hydrolysis of any ester, orthoester or amide formed affords the corresponding α-arylalkanoic acid.

In particular, the present invention comprises a process for preparing an α-arylalkanoic acid of the formula

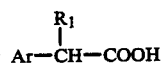

or an ester, orthoester or amide thereof wherein Ar is an aryl moiety, and $R_1$ is lower alkyl having 1–8 carbon atoms inclusive or cycloalkyl having 3–7 carbon atoms inclusive which comprises:

contacting a ketal or thioketal of a compound of the formula

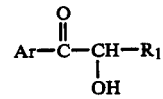

wherein Ar and $R_1$ are as defined above with an esterifying agent to form the corresponding ketal or thioketal ester substrate of a compound of the formula

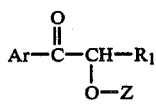

wherein Ar and $R_1$ are as defined above and —O—Z is the anionic residue of an organic acid and is sufficiently labile to disassociate from the ester substrate upon contacting with a protic or dipolar, aprotic solvent or mixtures thereof, maintaining the ester substrate in contact with the protic or dipolar, aprotic solvent for a time sufficient to form the α-arylalkanoic acid or ester, orthoester or amide corresponding, and optionally concomitantly or sequentially hydrolyzing any ester, orthoester or amide formed to the corresponding α-arylalkanoic acid.

In a further aspect, the process of the present invention comprises contacting a ketal of a compound of the formula

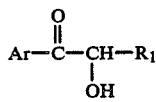

wherein Ar is an aryl moiety and $R_1$ is a lower alkyl having 1–8 carbon atoms inclusive or cycloalkyl having 3–7 carbon atoms inclusive with a source of sulfonyl ion, such as provided by an alkyl, alkenyl, alkynyl, cycloalkyl, aryl or aralkyl sulfonyl group, to form the corresponding sulfonate ester, maintaining the formed sulfonate ester in contact with a protic or dipolar, aprotic solvent or a mixture thereof for a time sufficient to form the corresponding α-arylalkanoic acid or ester, orthoester or amide thereof, and optionally concomitantly or sequentially hydrolyzing any ester, orthoester or amide formed to the corresponding α-arylalkanoic acid.

In another aspect, the invention comprises contacting an α-halo alkyl aryl ketone of the formula

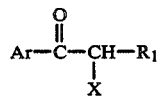

wherein Ar and $R_1$ are as defined above and X is halo with a strong base, such as an alkali metal aryloxide or alkoxide, to form the corresponding α-hydroxy ketal of the formula

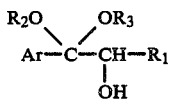

wherein $R_2$ and $R_3$ are independently the aryl or alkyl residues of the aryloxide or alkoxide, contacting the α-hydroxy ketal with a source of sulfonyl ion, such as provided by an alkyl, alkenyl, alkynyl, cycloalkyl aryl or aralkyl sulfonyl group, to form the corresponding sulfonate ester, and maintaining the sulfonate ester in contact with a protic or dipolar, aprotic solvent or a mixture thereof for a time sufficient to form the corresponding α-arylalkanoic acid or ester, orthoester or amide thereof, and optionally concomitantly or sequentially hydrolyzing any ester, orthoester or amide formed to the corresponding acid.

In a most particular aspect, the present invention comprises a process for preparing a compound of the formula

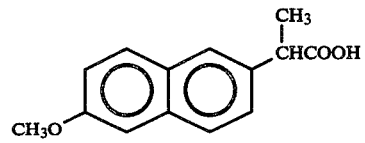

or an ester, orthoester or amide thereof which comprises contacting an α-hydroxy ketal of the formula

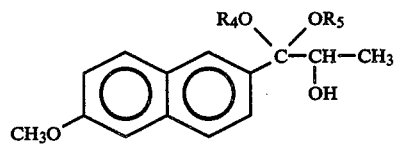

wherein $R_4$ and $R_5$ are lower alkyl having 1–4 carbon atoms inclusive, with a lower alkyl sulfonyl halide, to form the corresponding sulfonate ester of the formula

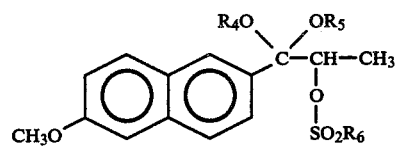

wherein $R_4$ and $R_5$ are as defined above and $R_6$ is lower alkyl having 1–4 carbon atoms inclusive, maintaining the sulfonate ester in contact with a protic or dipolar, aprotic solvent or a mixture thereof, preferably methanol-water, for a time sufficient to form, 2-(6-methoxy-2-naphthyl)propionic acid, represented by the structural formula

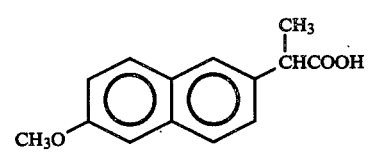

or an ester, orthoester or amide thereof and optionally concomitantly or sequentially hydrolyzing any ester, orthoester or amide formed to the corresponding acid.

In yet another aspect, the invention comprises ketal intermediates of the formula

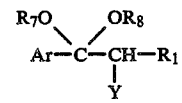

wherein Ar is as defined above, $R_1$ is as defined above, $R_7$ and $R_8$ are independently lower alkyl having 1–8 carbon atoms inclusive or when taken together methylene or ethylene, and Y is alkyl, alkenyl, alkynyl, cycloalkyl, aryl or aralkyl sulfonyloxy.

In still another aspect, the invention comprises ketal intermediates of the formula

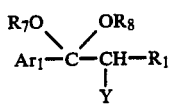

wherein $Ar_1$ is phenyl, phenoxyphenyl, naphthyl or biphenyl, each of those groups being optionally substituted by lower alkyl, halo or lower alkoxy, Y is hydroxy or is as defined above and $R_1$, $R_7$ and $R_8$ are as defined above, with the provision that when Y is hydroxy, $Ar_1$ is phenoxyphenyl, biphenyl or naphthyl, optionally substituted by lower alkyl, halo or lower alkoxy.

In another aspect, the invention comprises ketal intermediates of the formulae

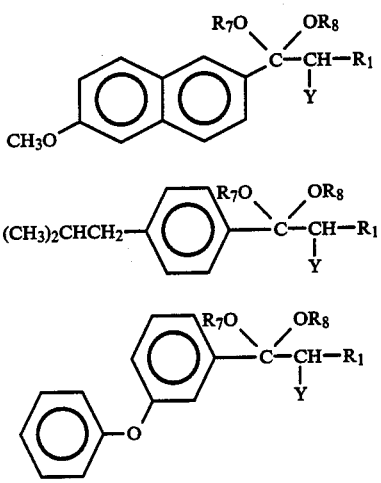

wherein $R_1$, $R_7$ and $R_8$ are as defined above and Y is hydroxy or alkyl, cycloalkyl, alkenyl, alkynyl, aryl or aralkyl sulfonyloxy.

DETAILED DESCRIPTION OF THE INVENTION

The process of the present invention utilizes as starting materials α-hydroxy ketals or thioketals of compounds of the formula

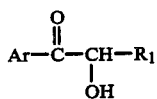

wherein Ar is an aryl moiety of a useful acid product and $R_1$ is a lower alkyl radical having from 1-8 carbon atoms inclusive or a cycloalkyl radical having from 3-7 carbon atoms inclusive. The lower alkyl radicals are exemplified by methyl, ethyl, propyl, butyl and octyl and the branched-chain isomers thereof. Representative of the cycloalkyl radicals are cyclopropyl, cyclobutyl, cyclopentyl, cyclohexyl and cycloheptyl. Those starting materials wherein $R_1$ is lower alkyl having 1-4 carbon atoms, and particularly methyl, are presently preferred. The aryl moieties as represented by Ar are exemplified particularly by those moieties disclosed in U.S. Pat. Nos. 3,385,386; 3,660,437; 3,624,142; 3,755,427; 3,904,682; 3,912,748 and Belgian Patent No. 747,812. In particular, Ar is exemplified by substituted or unsubstituted phenyl, phenoxyphenyl, naphthyl or biphenyl groups, such as represented by 3-phenoxyphenyl, 2-fluoro-1,1'-biphenyl, 4-isobutylphenyl, 4'-fluoro-4-biphenyl and 6-methoxy-2-naphthyl, and 4-chlorophenyl-5-benzoxyazoyl. The optional substituents on the phenyl, phenoxyphenyl, naphthyl and biphenyl groups are exemplified by lower alkyl having 1-4 carbon atoms inclusive, halo as exemplified by bromo, iodo, chloro and fluoro, and lower alkoxy groups having 1-4 carbon atoms inclusive as exemplified by methoxy, ethoxy, propoxy and butoxy and the branched-chain isomers thereof. Other non-interfering substituents can be present as well.

The α-hydroxy ketals are prepared from known or readily prepared α-halo alkyl aryl ketones of the formula

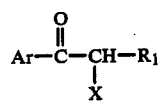

wherein Ar, $R_1$ are as defined hereinbefore and X is halo, exemplified by bromo, chloro and iodo. Methods of preparation of the α-halo alkyl aryl ketones have been described previously in British Patent Application Serial No. 8005752, filed Feb. 20, 1980, and published under No. 2,042,543 on Sept. 24, 1980. Methods of preparation of alkyl aryl ketone precursors of the α-halo alkyl aryl ketones have been described in U.S. Pat. No. 4,135,051. Such alkyl aryl ketone precursors can be conventionally halogenated by methods known in the art, such as described in the above-identified British Patent Application Serial No. 8005752 and *Reagents for Organic Synthesis*, 161 (John Wiley & Sons, Inc. 1967).

The α-hydroxy ketals are prepared from the α-halo alkyl aryl ketones of the above-described formula by contacting an α-halo alkyl aryl ketone with strong base in an alcoholic solvent medium. Such a method has been described previously in *J. Am. Chem. Soc.*, 72, 4758 (1950). Conveniently, an α-halo alkyl aryl ketone is contacted with an alkali metal salt of an aryloxide or alkoxide anion in a lower alkanol to afford the desired α-hydroxy ketals. The lower alkanols include the $C_1$-$C_8$ alkanols and their branched chain isomers and are exemplified by methanol, ethanol, n-propanol, isopropanol, hexanol, octanol and the like. Other non-interfering organic solvents such as benzene and toluene can be present as well. The alkali metals are exemplified by sodium, potassium and lithium and the aryloxide and alkoxide anions are exemplified by phenoxide, methoxide, ethoxide and the like. In the above described process, the α-hydroxy ketal is formed in a one-step process. Equivalently, the cyclic ketal or thioketal could be formed by exchange from the dialkoxy or diaryloxy ketals.

For example, 2-bromo 1-(6-methoxy-2-naphthyl)propan-1-one is treated with sodium methoxide in methanol to afford the α-hydroxy ketal, 1,1-dimethoxy-1-(6-methoxy-2-naphthyl)propan-2-ol.

The α-hydroxy ketal or thioketal of the alkyl aryl ketone then is treated with an esterifying agent to form the corresponding ketal or thioketal ester substrate of a compound of the formula

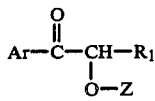

$$Ar-\overset{O}{\underset{\underset{O-Z}{|}}{\overset{\|}{C}}}-CH-R_1$$

wherein Ar and $R_1$ are as defined above and —O—Z is the anionic residue of an organic acid and is sufficiently labile to disassociate from the substrate upon contact with a protic or dipolar aprotic solvent medium. Particularly suitable organic acids are those having electron deficient substituents such as exemplified by aryl, aralkyl, cycloalkyl, alkyl, alkenyl and alkynyl sulfonic acids and substituted benzoic acids.

Included among the group comprehended by alkyl (including straight and branched chain groups) are those exemplified by methyl, ethyl, propyl, isopropyl, n-butyl, sec-butyl, tert-butyl, amyl, hexyl, heptyl, octyl, decyl, dodecyl and octadecyl. Representative of the alkenyl groups are vinyl, allyl, methallyl, butenyl, pentenyl, hexenyl, heptenyl, octenyl and isomeric forms thereof. Typical of the alkynyl groups are propynyl, butynyl, pentynyl, hexynyl, heptynyl, octynyl and isomeric forms thereof. Representative of the cycloalkyl groups are cyclobutyl, cyclopentyl, cyclohexyl, 1-cyclohexenyl, methylcyclohexyl, cycloheptyl, cyclooctyl, cyclodecyl, cycloundecyl, cyclododecyl and cyclopentadecyl. The aryl and aralkyl groups are exemplified by tolyl, xylyl, benzyl, phenethyl, phenylpropyl, benzhydryl, naphthylmethyl, and the like, as well as fused and bridged ring structures, such indanyl, indenyl, naphthyl, acenaphthyl, phenanthryl, cyclopentanopolyhydrophenanthryl, adamantanyl, bicyclo[3:1:1]heptyl, bicyclo[2:2:2]octyl and the like. All of the above can either be unsubstituted or substituted with one or more non-interfering substituents, such as hydroxyl derivatives, for example, alkoxy such as methoxy, ethoxy, propoxy, butoxy, and the like; acyloxy, such as acetoxy, propionoxy, butyroxy and the like; nitro groups; alkylamino groups, such as dimethylamino, diethylamino and the like; halogens, such as fluorine, chlorine, or bromine; carbonyl derivatives such as enol ethers and ketals; and the like.

Presently preferred sulfonic acids are the alkylsulfonic acids such as methanesulfonic acid and the aryl and aralkyl sulfonic acids such as toluenesulfonic acid, benzenesulfonic acid, camphorsulfonic acid and β-styrenesulfonic acid. Various polymeric sulfonic acids such as polymeric alkyl and aryl sulfonic acids can also be utilized.

Other organic acids having electron-deficient substituents, the anions of which form sufficiently labile ester leaving groups which disassociate from the substrate upon contacting with a protic or dipolar, aprotic solvent medium could be used as well. The esterifying agent typically comprises the acid halide, such as the chloride, bromide, or iodide, of the described organic acids. The acid chlorides are presently preferred. The foregoing esterification of the α-hydroxy alkyl aryl ketal or thioketal to the corresponding ester substrate is exemplified by the contacting of 1,1-dimethoxy-1-(6-methoxy-2-naphthyl)-propan-2-ol with methanesulfonyl chloride in triethylamine to form the corresponding 1,1-dimethoxy-1-(6-methoxy-2-naphthyl)prop 2-yl methanesulfonate. The esterification step is conveniently conducted in organic bases such as pyridine, tertiary alkylamines such as trimethylamine, triethylamine, lutidine, N-methylmorpholine, N,N-dimethylaniline, and the like or inert organic solvents, such as halogenated hydrocarbons (e.g. methylene chloride), hexane, toluene, xylene and the like, containing an organic base of the type described.

The resulting ester then is maintained in contact with a protic or dipolar, aprotic solvent for a time sufficient to form the α-aryl alkanoic acid or the ester, orthoester or amide thereof. The protic solvents comprehended include water, alcohols, ammonia, amides, N-alkyl amides, carboxylic acids and mixtures thereof.

Representative alcohols include primary, secondary and tertiary alcohols and polyhydric alcohols. They include alkanols, alkenols, cyclic alkanols, phenols, glycols, and the like. Examples of the alkanols comprehended are methanol, ethanol, butanol, pentanol, hexanol, heptanol, octanol, and the branched chain isomers thereof. Examples of the alkenols are allyl alcohol, 2-buten-1-ol and the like. Cyclic alkanols are exemplified by cyclopropanol, cyclobutanol, cyclohexanol and the like. Examples of phenols are phenol, α-naphthol, β-naphthol, p-cresol and the like. Representative amides are formamide, acetamide, propionamide, benzamide and the like. Typical of the N-alkyl amides are N-methylformamide, N-ethylformamide, N-carboxylic acids are alkanoic acids such as formic acid, acetic acid, proponic acid, n-butyric acid and the branched chain isomers thereof, alkenoic acids, such as acrylic acid, maleic acid and fumoric acid and the like aryl acids such as benzoic acid, phthalic acid and isophthalic acid and the like, and diacids such as malonic, succinic, glutaric and the like.

Dipolar, aprotic solvents are typified by dimethylsulfide, acetone, 2,3-dioxane, carbon disulfide, dialkylamides such as dimethylacetamide and dimethylformamide, nitrobenzene, nitromethane, acetonitrile and the like and mixtures thereof.

The rate of the rearrangement reaction appears to be inhanced by the presence of salts of organic or inorganic anions. For example, the addition of sodium acetate or sodium bicarbonate to the reaction mixture facilitates the reaction. Additionally, it is desirable to buffer the solvent medium to prevent hydrolysis of the ketal or thioketal prior to occurence of the rearrangement. Typical buffering salts include the sodium, potassium and lithium salts of carbonate, bicarbonate, anions of organic acids and phosphates.

Depending on the nature of the protic or dipolar aprotic solvent medium, the α-arylalkanoic acid may not be directly formed. Instead, the ester, orthoester or amide of the α-arylalkanoic acid may be formed. For example, if the solvent medium contains water, an ester of the α-arylalkanoic acid typically is formed wherein the ester group is derived from the ketal functionality or from the solvent. Mixed esters can be formed. Under anhydrous alcoholic conditions, orthoesters of the α-arylalkanoic acid can be formed wherein the ester groups may be derived from the ketal functionality or from the solvent and may be mixed. Likewise, when an amine is present in the solvent medium, formation of an amide of the α-arylalkanoic acid can be expected. Those compounds typically are not isolated but are hydrolyzed directly to the desired α-arylalkanoic acid. Depending on the reaction conditions, hydrolysis may be effected concommitantly or sequentially by standard methods. For example, when the protic solvent medium comprises acetic acid and sodium acetate and the ester substrate comprises 1,1-dimethoxy-1-(6-methoxy-2- naphthyl)prop-2-yl methanesulfonate, there is afforded the compound, methyl 2-(6-methoxy-2-naphthyl)propionate. The methyl ester is then sequentially hydrolyzed to the corresponding acid by contact with base. Alternatively, the α-arylalkanoic acid can be obtained by concomitantly hydrolysis by maintaining the ester substrate in contact with a methanol-water solution containing sodium bicarbonate. Typically, 1,1-dimethoxy-1-(6-methoxy-2-naphthyl)-prop-2-yl methanesulfonate is maintained in contact with a methanol-water solution containing sodium bicarbonate to afford 2-(6-methoxy-2-naphthyl)propionic acid.

The process of the present invention is advantageous in another aspect in that the α-hydroxy ketal or thioketal can be resolved to afford the optically active enantiomers. The resolution can be effected by conventional methods for resolving alcohols which are well known in the art. Separation of the enantiomers and regeneration of the α-hydroxy substituent yields an optically active material which can subsequently be utilized in the process as hereinbefore described.

As the rearrangement of the aryl group is considered to take place with inversion of configuration at the carbon atom attached to the dissociating ester group, the appropriate enantiomer is chosen to afford an α-arylalkonic acid of the desired optical enrichment which is most advantageous pharmaceutically, if one of the enantiomers of the acid product is pharmaceutically more active or advantageous than the other.

For example, in the preparation of 2-(6-methoxy-2-naphthyl)propionic acid, the (S)-form (i.e. d(+)) is desirable and the (S)-form of the optically active α-hydroxy ketal or thioketal would be considered an appropriate starting material.

Alternatively, the racemic α-arylalkanoic acids produced hereby can be resolved by known methods to afford a desired optically active product. For example, racemic 2-(6-methoxy-2-naphthyl)propionic acid can be resolved by methods described in U.S. Pat. Nos. 3,904,683, 4,246,164 and 4,246,193.

Reaction times, temperatures and material ratios for conducting the process of this invention are not considered critical. However, it has been found convenient to conduct the ketalization step in the temperature range of between −10° C. and the refluxing temperature of the reaction mixture. Typical reaction times are between 0.5 to 10 hours. Suitable yields have been obtained by utilizing an excess of the alkali metal alkoxides and aryloxides, such as in the range of 1.1–2.5 equivalents. The esterification step is conveniently conducted between −10° C. and the refluxing temperature of the reaction mixture and for times ranging between 0.5–5 hours. The esterification agent, i.e. the acid halide, typically is present in 0–50% molar excess and the organic base in 0–100% molar excess. The solvolysis step in the protic or dipolar, protic solvent medium is conducted typically in a temperature range between 50°–200° C. and for times ranging between 1–100 hours. Various combinations of times, temperatures and material ratios can be chosen by those skilled in the art to optimize the various process steps utilized and exemplified herein.

The invention, is further exemplified by the embodiments described in the following illustrative and non-limiting examples.

EXAMPLE 1

A mixture of 4.2 g of 2-bromo-1-(6-methoxy-2-naphthyl)propan-1-one, 8.2 g of sodium methoxide and 50 ml of methanol is stirred at room temperature (28° C.) for about one hour. The resulting mixture is added to water and extracted with ether. The ethereal extract is dried over magnesium sulfate and evaporated to yield 1,1-dimethoxy-1-(6-methoxy-2-naphthyl)propan-2-ol as an oil. That compound displays a characteristic NMR spectra in deuterochloroform of τ=9.0 (doublet, J=2), 7.41 (doublet, J=1), 6.75, 6.58, 6.11, 5.8 (d,q multiplet, J=2, 1), 2–2.9 (multiplet).

EXAMPLE 2

1.2 G of 1,1-dimethoxy-1-(6 methoxy-2-naphthyl)-propan 2-ol is dissolved in 10 ml of pyridine and 1.1 g of methanesulfonyl chloride is added to that solution in one portion. The mixture is allowed to stand for about three hours and the separation of pyridine hydrochloride crystals is observed. The reaction mixture is poured into 100 ml of water and extracted with 50 ml of ether. The ethereal extract is washed several times with water and dried over magnesium sulfate. The ethereal layer is evaporated under reduced pressure to afford 1,1-dimethoxy-1-(6-methoxy-2-naphthyl)prop-2-yl methanesulfonate as an oil. The compound displays a characteristic NMR spectra in the deuterochloroform of τ=9.0 (doublet, J=2), 6.85, 6.70, 6.61, 6.07, 4.89 (quartet, J=2), 1.99–2.88 (multiplet).

EXAMPLE 3

The oil obtained in Example 2 is mixed with 25 ml of glacial acetic acid and 0.5 g of sodium acetate, heated to 60° C. for three hours and maintained at 40° C. for 12 hours. After that time, the mixture is cooled and to it is added 200 ml of water. The mixture is extracted with ether and the ethereal layer is washed with water and sodium bicarbonate until neutral. Then the ethereal layer is dried over magnesium sulfate and evaporated under reduced pressure to yield methyl 2-(6-methoxy-2-naphthyl)propionate as an oil.

EXAMPLE 4

A mixture containing 1.4 g of 1,1-dimethoxy-1-(6-methoxy-2-naphthyl)prop-2-yl methanesulfonate, 4.0 g of sodium acetate and 20 ml of glacial acetic acid is heated to 95°–100° C. for four hours. The reaction mixture is cooled and poured into water, extracted with ether, and the ethereal extracts are washed successively with sodium bicarbonate and water and dried over magnesium sulfate. The ethereal layer is evaporated under reduced pressure to yield methyl 2-(6-methoxy-2-naphthyl)propionate as an oil.

EXAMPLE 5

A slurry of 22.5 g of 2-bromo-1-(6-methoxy-2-naphthyl)propan-1-one in 250 ml of methanol is cooled to 10° C. and treated with 9.7 g of sodium methoxide added as a solid over a period of about 10 minutes. The reaction mixture is stirred at 15° C. for about 10 minutes and allowed to warm to 20° C. at which temperature it is stirred for an additional 15 minutes. Then the reaction mixture is poured into 250 ml of water and extracted with 250 ml of methylene chloride. The organic layer is separated, filtered and dried over magnesium sulfate. Upon evaporation under reduced pressure, there is obtained 22 g of 1,1-dimethoxy-1-(6-methoxy-2-naphthyl)propan-2-ol, as an oil.

EXAMPLE 6

The crude oil, 1,1-dimethoxy-1-(6-methoxy-2-naphthyl)propan-2-ol, from Example 5 is dissolved in 250 ml of methylene chloride and cooled to 10° C. Then 12.2 g of trimethylamine is added and the reaction mixture is cooled to about 5° C. Over a 15 minute period, 10.55 g of methanesulfonyl chloride is added. The reaction mixture is stirred for about 30 minutes at 0°–5° C. Separation of the triethylamine hydrochloride as a precipitate is observed. The reaction mixture then is poured into 200 ml of water and extracted with methylene chloride. The organic phase is separated, dried over magnesium sulfate and evaporated under reduced pressure to yield 1,1-dimethoxy-1-(6-methoxy-2-naphthyl)-prop-2-yl methanesulfonate as an oil.

EXAMPLE 7

The oil, 1,1-dimethoxy-1-(6-methoxy-2-naphthyl)-prop-2-yl methanesulfonate, from Example 6 and 4.9 g of sodium acetate is dissolved in 200 ml of glacial acetic acid. The mixture is heated to 90°–100° C. and maintained at that temperature for approximately 3 hours. An additional 3.8 g of sodium acetate is added to the reaction mixture and the mixture is stirred for an additional three hours. The reaction mixture then is heated to 100° C. where it is held for an additional three hours. After that time 200 ml of methylene chloride and 50 ml of water is added to the reaction mixture. The organic and aqeuous layers are separated and the organic layer is evaporated under reduced pressure to afford methyl 2-(6-methoxy-2-naphthyl)propionate. The resulting methyl 2-(6-methoxy-2-naphthyl)propionate is hydrolyzed with a mixture of methanol/potassium hydroxide-water. The reaction mixture is poured into water and extracted with methylene chloride to afford the acid, 2-(6-methoxy-2-naphthyl)propionic acid (melting point: 153°–155° C.).

EXAMPLE 8

11.4 G of sodium methoxide is added to a slurry of 25.5 g of 2-bromo-1-(6-methoxy-2-naphthyl)propan-1-one in 200 ml of methanol at 10° C. The addition of the sodium methoxide takes place over approximately a 30 minute period during which the reaction mixture is allowed to warm. Then the mixture is stirred for about 1 hour at room temperature and the methanol is stripped from the mixture at 50° C. on a rotary evaporator until approximately 80% of the methanol has been removed. The resulting reaction mixture is quenched in water and extracted with methylene chloride. The organic layer is separated, dried over magnesium sulfate and evaporated under reduced pressure to afford 23.3 g of 1,1-dimethoxy-1-(6-methoxy-2-naphthyl)propan-2-ol as an oil.

EXAMPLE 9

The crude oil, 1,1-dimethoxy-1-(6-methoxy-2-naphthyl)propan-2-ol, from Example 8 is dissolved in 200 ml of methylene chloride and to that mixture is added 13.2 g of triethylamine. The reaction mixture is cooled to 5° C. and 11.0 g of methanesulfonyl chloride is added slowly, maintaining the temperature between 5°–10° C. The precipitation of triethylamine hydrochloride crystals is observed. After the addition of the methanesulfonyl chloride has been completed, the reaction mixture is stirred for an additional one-half hour. Then the solution is filtered to remove the triethylamine hydrochloride crystals and the filtrate is poured into 200 ml of water. The organic layer is separated and dried over magnesium sulfate. Evaporation of the organic layer under reduced pressure yields 30.4 g of crude 1,1-dimethoxy-1-(6-methoxy-2-naphthyl)prop-2-yl methanesulfonate as an oil.

EXAMPLE 10

The crude oil, 1,1-dimethoxy-1-(6-methoxy-2-naphthyl)prop 2-yl methanesulfonate, from Example 9 is dissolved in 200 ml of glacial acetic acid. Then 10.2 g of sodium acetate is added and the mixture is heated to 110° C. The reaction mixture is maintained at that temperature for about 3 hours, after which time the acetic acid is removed under reduced pressure to yield an oily solid. 200 Ml of methylene chloride and 100 ml of water is added to the solid and the organic and aqueous layers are separated. The organic layer is washed with water and sodium bicarbonate until neutral and then dried over magnesium sulfate. Reduction of the organic layer under reduced pressure affords 19.6 g of crude methyl 2-(6-methoxy-2-naphthyl)propionate.

The crude methyl 2-(6-methoxy-2-naphthyl)propionate is hydrolyzed with methanol/potassium hydroxide/water until TLC indicates no remaining ester. Then the reaction mixture is poured into water and extracted with methylene chloride and acidified with hydrochloric acid. The mixture is filtered and the organic and aqueous layers are separated. The aqueous layer then is acidified and filtered to yield 13.5 g of 2-(6-methoxy-2-naphthyl)propionic acid (melting point: 153°–155° C.).

EXAMPLE 11

3.1 G of 2-bromo 1-(6-methoxy-2-naphthyl)propan-1-one is dissolved in 15 ml of toluene and 15 ml of methanol. To that solution is added a solution of methanol-sodium methoxide prepared from 12 ml of methanol added to sodium metal and utilizing the resulting clear solution. The methanol-sodium methoxide solution is added slowly at 20°–25° C. until all the bromo ketone has reacted. The toluene-methanol azeotrope present in the reaction mixture is stripped under reduced pressure and replaced by toluene. The precipitated salts are separated by filtration and the solution containing 1,1-dimethoxy-1-(6-methoxy-2-naphthyl)propan-2-ol is used subsequently.

EXAMPLE 12

1.7 G of triethylamine is added to 40 ml of the toluene solution from Example 11 containing 1,1-dimethoxy-1-(6-methoxy-2-naphthyl)propan-2-ol, and the reaction mixture is cooled to about 8° C. Then 1.5 g of methanesulfonyl chloride is added slowly. The reaction is exothermic and is completed quickly. The triethylamine hydrochloride salts are removed by filtration at 10° C. and the excess trimethylamine is distilled under vacuum at about 60°–65° C. The remaining toluene solution is evaporated under reduced pressure on a rotary evaporator to yield 1,1-dimethoxy-1-(6-methoxy-2-naphthyl)-prop 2-yl methanesulfonate as an oil.

EXAMPLE 13

The oil from Example 12 containing 1,1-dimethoxy-1-(6-methoxy-2-naphthyl)prop-2-yl methanesulfonate is dissolved in 40 ml of glacial acetic acid containing 3 g of sodium acetate. The solution then is heated to 110° C. and maintained at that temperature for approximately 2 hours. The resulting mixture is poured into water and extracted with ether to yield, after washing with water containing sodium bicarbonate, the compound methyl 2-(6-methoxy-2-naphthyl)propionate.

EXAMPLE 14

A mixture containing 1.6 g of 1,1-dimethoxy-1-(6-methoxy-2-naphthyl)prop 2-yl methanesulfonate, 1.5 g of sodium bicarbonate, 10 ml of water and 10 ml of methanol is heated at 70° C. with refluxing for 1½ hours. Then the reaction mixture is cooled and poured into water and extracted with ether. The ethereal extract is dried over magnesium sulfate and evaporated under reduced pressure to yield 1.07 g of 2-(6-methoxy-2-naphthyl)propionic acid.

EXAMPLE 15

A sodium methoxide solution prepared by adding 3.2 g of sodium to 40 ml of methanol at 10° C. is added slowly to a solution of 20 g of 2-bromo-1-(6-methoxy-2-naphthyl)-propan-1-one in 100 ml of methanol, and 100 ml of toluene is added. The addition takes place over about a one-hour period and the reaction mixture is stirred and allowed to warm for 1½ additional hours. Then the reaction mixture is poured into water, and extracted with toluene-ether. The organic phase is separated, dried and evaporated to afford 1,1-dimethoxy-1-(6-methoxy-2-naphthyl)propan-2-ol as an oil.

EXAMPLE 16

The oil, 1,1-dimethoxy-1-(6-methoxy-2-naphthyl)-propan-2-ol, prepared in Example 15 is dissolved in 200 ml of toluene, cooled to about 10° C., and to that solution is added 10.5 g of triethylamine. Then 8.5 g of methanesulfonyl chloride is added dropwise to the solution and an exothermic reaction is noted along with the precipitation of triethylamine hydrochloride crystals. The addition occurs over about a 45 minute period and the solution is allowed to warm to about 20° C. Then the reaction mixture is poured into water and extracted with toluene-ether. The organic extracts are separated, dried over magnesium sulfate and evaporated to yield 1,1-dimethoxy-1-(6-methoxy-2-naphthyl)prop-2-yl methanesulfonate as an oil.

EXAMPLE 17

A mixture is prepared from the oil, 1,1-dimethoxy-1-(6-methoxy-2-naphthyl)prop-2-yl methanesulfonate, from Example 16, 20 g of sodium bicarbonate, 200 ml of methanol and 150 ml of water, and the mixture is heated at 70° C. with reflux for 14 hours. The methanol is removed under reduced pressure on a rotary evaporator and the oil remaining is extracted with ethyl ether. The organic and aqueous phases are separated and the aqueous phase is acidified with hydrochloric acid to afford 12.5 g of 2-(6-methoxy-2-naphthyl)propionic acid.

EXAMPLE 18

To a mixture of 74.91 g of anhydrous aluminum trichloride and 300 ml of dry methylene chloride, maintained at about −10° C. in a salt-ice bath, is added a mixture of 67.1 g of isobutylbenzene and 46.77 g of propionyl chloride over a 90 minute period, while maintaining the temperature at between about −5° C. to 0° C. The reaction mixture then is stirred for an additional 30 minutes, quenched with a dilute hydrochloric acid solution and extracted with methylene chloride. The aqueous layer is separated and extracted twice more with methylene chloride and then the combined methylene chloride extracts are washed with water and saturated sodium bicarbonate. The organic extracts then are dried over magnesium sulfate, filtered and the methylene chloride is removed on a rotary evaporator to yield 1-(4-isobutylphenyl)propan-1-one.

EXAMPLE 19

A mixture of 38 g of 1-(4-isobutylphenyl)propan-1-one, 93.5 g of cupric bromide and 250 ml of ethyl acetate is heated to 50° C. After stirring at 50° C. for about 1 hour, the mixture is heated to reflux (71°–72° C.) and stirring is continued for approximately 6 hours. After that time, the mixture is allowed to cool and is stirred overnight. The reaction mixture then is filtered and the filter cake is washed with ethyl acetate. The filtrates are collected and washed with 3% ammonium hydroxide and saturated sodium chloride solution. The washes are reextracted with ethyl acetate. Then the ethyl acetate extracts are washed with an aqueous saturated sodium chloride solution and the ethyl acetate extracts are dried over magnesium sulfate. After filtering, the solvent is removed on a rotary evaporator under reduced pressure to afford crude 2-bromo 1-(4-isobutylphenyl)propan-1-one.

EXAMPLE 20

A mixture of 13.46 g of 2-bromo 1-(4-isobutylphenyl)-propan-1-one in 60 ml of methanol is treated with a sodium methoxide solution prepared from 2.88 g of freshly cut sodium metal being dissolved in 60 ml of dry methanol dropwise over about a 30 minute period, while maintaining the reaction mixture at a temperature between about 15°–25° C. After the addition has been completed, the reaction mixture is stirred for another 30 minutes at about 20°–25° C. The reaction mixture then is poured over ice and extracted four times with ethyl ether. The ethereal extracts are washed with saturated sodium chloride and dried over sodium sulfate. After filtration to remove the sodium sulfate, the solvent is removed under reduced pressure on a rotary evaporator. 12.37 G of 1-(4-isobutylphenyl)-1,1-dimethoxypropan-2-ol [which is characterized by an NMR spectra in deuterochloroform of $\tau=9.14$ (doublet, J=2.2), 9.04 (doublet, J=2), 8.09 (septet, J=2.1), 7.59 (doublet, J=1.7), 6.79, 6.61, 7.51 (doublet, J=2.3), 5.9 (d,q multiplet, J=2.2, 1.7) and 2.5–2.9 (aromatic AB pattern)] is obtained.

EXAMPLE 21

A solution of 6.25 g of methanesulfonyl chloride in 20 ml of dry methylene chloride is added dropwise to a mixture of 12.37 g of 1-(4-isobutylphenyl)-1,1-dimethoxypropan-2-ol and 80 ml of dry methylene chloride containing 6.5 g of dry triethylamine at 5°–10° C. The addition takes place over about 40 minutes and the reaction mixture is stirred for an additional 1.5 hours at 5°–10° C. after that addition is completed. After that time, an additional 0.6 g of methanesulfonyl chloride is added at 5°–10° C. and stirring is continued for an additional 50 minutes. An additional 1.5 g of triethylamine is added to the reaction mixture and then the reaction mixture is poured into 50 ml of water. The aqueous and organic phases are separated and the aqueous phase is extracted with methylene chloride. The combined methylene chloride layers then are washed with 50 ml of saturated aqueous sodium chloride and the methylene chloride layer is dried over sodium sulfate. After filtration to remove the sodium sulfate, the methylene chloride is evaporated on a rotary evaporator under reduced pressure to afford 1-(4-isobutylphenyl)-1,1-dimethoxyprop-2-yl methanesulfonate [which is characterized by an NMR spectra in deuterochloroform of $\tau=9.10$ (doublet, J=2.2), 8.8 (doublet, J=2.1), 8.12 (septet, J=2.1), 7.48 (doublet, J=2.3), 6.88, 6.75, 6.67, 4.92 (quartet, J=2.1) and 2.5–2.9 (aromatic AB pattern)].

EXAMPLE 22

A mixture of 17 g of 1-(4-isobutylphenyl)-1,1-dimethoxyprop-2-yl methanesulfonate from Example 21, 16.5 g of sodium bicarbonate, 170 ml of methanol and 135 ml of water is heated to 67°–70° C. and held at reflux for 23 hours. Then the methanol is distilled from the reaction mixture and the aqueous phase remaining is extracted with 150 ml of methylene chloride. The aqueous phase is acidified with concentrated hydrochloric acid and extracted with 150 ml of methylene chloride. The organic phase is dried over magnesium sulfate, and the solvent evaporated to yield 7.67 g of 2-(4-isobutylphenyl)propionic acid (melting point: 73°–75° C.).

EXAMPLE 23

A mixture of 25.1 g of 3-phenoxybenzaldehyde in 23 ml of an anhydrous tetrahydrofuran is added dropwise to 60 ml of 3-N-ethylmagnesium bromide in ethyl ether, cooled in an ice bath under a nitrogen atmosphere, over a period of about 1½ hours. The reaction mixture is stirred overnight and warmed to room temperature, after which time it is poured over ice containing 12 ml of acetic acid. The organic and aqueous phases are separated and the aqueous phases extracted twice with ethyl ether. The ethereal extracts are combined and washed with a solution prepared from 3 g of sodium carbonate and 40 ml of water. The aqueous wash layers are extracted further with ethyl ether and the combined ethereal extracts are dried over anhydrous sodium sulfate and filtered. The ether is removed under reduced pressure to yield 29.45 g of 1-(3-phenoxyphenyl)propan-1-ol.

EXAMPLE 24

A solution of 35 g of 1-(3-phenoxyphenyl)propan-1-ol and 50 ml of ethyl ether is treated with 1.1 equivalants of chromic acid, which is added dropwise over a 30 minute period. The reaction mixture is allowed to warm to 20°–25° C. and stirred for about 2 hours. Then the reaction mixture is added to a mixture of 25 ml of ethyl ether and 50 ml of water, and sodium carbonate is slowly added to neutralize the acid. The phases are separated and the aqueous phase is reextracted twice with ethyl ether. The ethereal extracts are combined and evaporated under reduced pressure to yield 1-(3-phenoxyphenyl)-propan-1-one as an oil.

EXAMPLE 25

A mixture containing 26.36 g of 1-(3-phenoxyphenyl)-propan-1-one, 54.66 g of cupric bromide, and 145 ml of ethyl acetate is heated under a nitrogen atmosphere with stirring to 50° C. and maintained at that temperature for approxiately 1½ hours. Then the mixture is heated to reflux and maintained at reflux for approximately 3 hours. Heating is stopped and the reaction mixture is allowed to stir overnight at room temperature. Then the reaction mixture is filtered to remove the formed cuprous bromide and the filtrate is washed twice with 3% ammonium hydroxide solution and once with saturated sodium chloride solution. The aqueous washes are extracted again with 50 ml of ethyl acetate. The ethyl acetate layers are combined and dried over magnesium sulfate. After filtering to remove the magnesium sulfate, the solvent is removed under reduced pressure to afford 36.7 g of 2-bromo-1-(3-phenoxyphenyl)propan-1-one as an oil.

EXAMPLE 26

A solution of sodium methoxide is prepared from 5.09 g of sodium metal dissolved in 70 ml of methanol. That solution is added to 20.4 g of 2-bromo-1-(3-phenoxyphenyl)propan-1-one in 80 ml of methanol, maintained at 20°–25° C., over a period of 30 minutes. After the addition is completed, the reaction mixture is stirred at 25° C. for 50 minutes and poured into 250 ml of ice water. The resulting suspension is extracted with 30 ml of ethyl ether and the organic phase dried over magnesium sulfate. The solvent is evaporated under reduced pressure to yield 19.8 g of 1,1-dimethoxy-1-(3-phenoxyphenyl)propan-2-ol as an oil.

EXAMPLE 27

The oil, 1,1-dimethoxy-1-(3-phenoxyphenyl)-propan-2-ol, from Example 26 and 11.3 g of triethylamine are dissolved in 65 ml of toluene. Then the solution is cooled to 10°–12° C. and 9.7 g of methanesulfonyl chloride in 35 ml of toluene is added over 30 minutes. After the addition is completed, the mixture is poured into 100 ml of saturated sodium bicarbonate solution, and 100 ml of toluene is added. The organic layer is separated, dried over magnesium sulfate and evaporated to yield 23.25 g of 1,1-dimethoxy-1-(3-phenoxyphenyl)prop-2-yl methanesulfonate, as an oil.

EXAMPLE 28

The oil from Example 27, 1,1-dimethoxy-1-(3-phenoxyphenyl)prop-2-yl methanesulfonate, and 14.9 g of sodium acetate are dissolved in 200 ml of acetic acid and the resulting mixture is heated to reflux. After refluxing for four hours, the mixture is cooled to 25° C. and most of the acetic acid is removed by distillation. The residue is dissolved in 150 ml of ethyl ether and extracted several times with water. The ether is evaporated and replaced by 10 ml of methanol, 50 ml of water, and 7.5 g of sodium hydroxide. The resulting mixture is heated to reflux and refluxed for one hour. The methanol is removed by distillation and the resulting aqueous solution is extracted with 200 ml methylene chloride and acidified with hydrochloric acid. The suspension formed is extracted with 150 ml of methylene chloride and the organic layer is dried over magnesium sulfate. The solvent is removed to yield 4.04 g of 2-(3-phenoxyphenyl)-propionic acid [which is characterized by an NMR spectra in deuterochloroform of $\tau=8.54$ (doublet, J=2.5), 5.23 (quartet, J=2.5), 2.45–3.15 (multiplet), 1.5.]

EXAMPLE 29

A solution is prepared from 2.1 g of sodium metal and 15 ml of methanol. That solution then is added, dropwise, over a period of about 30 minutes, to a slurry of 10.4 g of 2-bromo-1-(6-methoxy-2-naphthyl)propan-1-one in 80 ml of methanol, maintained at about 20° C. The reaction mixture is poured into 5 volumes of water and extracted twice with 100 ml of ethyl ether. The ethereal layers are combined, dried over magnesium sulfate, and evaporated to yield 1,1-dimethoxy-1-(6-methoxy-2-naphthyl)propan-2-ol as an oil.

EXAMPLE 30

The oil, 1,1-dimethoxy-1-(6-methoxy-2-naphthyl) propan-2-ol, prepared in Example 29 is dissolved in 60 ml of pyridine and cooled to 10° C. Then 13 g of p-toluenesulfonyl chloride is added and the reaction mixture is stirred to dissolve the p-toluenesulfonyl chloride. The reaction mixture is allowed to stand overnight and the precipitation of pyridine hydrochloride is observed. The reaction mixture is poured into 7 volumes of water and extracted with ethyl ether. The ethereal layer is washed with dilute hydrochloric acid and then with dilute sodium hydroxide. The ethereal extract is dried over magnesium sulfate and evaporated to yield 1,1-dimethoxy-1-(6-methoxy-2-naphthyl)prop-2-yl p-toluenesulfonate, as an oil, [which is characterized by an NMR spectra in duterochloroform of $\tau=8.86$ (doublet, J=2.5), 7.57, 6.82, 6.74, 6.09, 4.87 (quartet, J=2.5), 2.2–3.0 (multiplet)].

EXAMPLE 31

A mixture of the oil, 1,1-dimethoxy-1-(6-methoxy-2-naphthyl)prop-2-yl p-toluenesulfonate, from Example 30, 50 ml of water, 100 ml of methanol and 19.5 g of sodium bicarbonate is refluxed (70° C.) for 14 hours. After that time, the mixture is cooled, poured into 6 volumes of water and extracted twice with 100 ml of toluene. The aqueous layer is acidified with concentrated hydrochloric acid to a pH of about 3 to yield 4.8 g of 2-(6-methoxy-2-naphthyl)propionic acid (melting point: 151.5°–153° C.).

EXAMPLE 32

By substituting an equivalent quantity of benzenesulfonyl chloride for the p-toluenesulfonyl chloride in the procedure of Example 30, and otherwise following the procedures of Examples 30 and 31, there is obtained 2-(6-methoxy-2-naphthyl)propionic acid.

EXAMPLE 33

By substituting an equivalent quantity of p-toluenesulfonyl chloride or benzenesulfonyl chloride for the methanesulfonyl chloride in Example 21 and Example 27, and otherwise sequentially following the procedures of Examples 21 and 22 and Examples 27 and 28, there is obtained, respectively, 2-4-(isobutylphenyl)-propionic acid and 2-(3-phenoxyphenyl)propionic acid.

What is claimed is:

1. A process for preparing an α-arylalkanoic acid of the formula

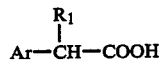

or an ester, orthoester or amide thereof wherein Ar is an aryl moiety, and $R_1$ is lower alkyl having 1–8 carbon atoms inclusive or cycloalkyl having 3–7 carbon atoms inclusive, which comprises:

contacting an α-halo alkyl aryl ketone of the formula

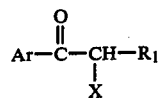

wherein Ar and $R_1$ are as defined above and X is halo with an alkali metal aryloxide or alkoxide to form the α-hydroxy ketal of the formula

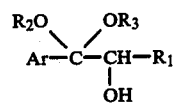

wherein $R_2$ and $R_3$ are the aryl or alkyl residues of the aryloxide or alkoxide groups, contacting the α-hydroxy ketal with a source of sulfonyl ion to form the corresponding sulfonate ester, and maintaining the sulfonate ester in contact with a protic or dipolar, aprotic solvent for a time sufficient to form the corresponding α-arylalkanoic acid or ester, orthoester or amide thereof and optionally concomitantly or sequentially hydrolyzing any ester, orthoester or amide formed to the corresponding acid.

2. The process of claim 1 wherein the source of sulfonyl ion is an alkylsulfonyl or an arylsulfonyl halide.

3. The process of claim 2 wherein $R_2$ and $R_3$ are methyl and the source of sulfonyl ion is methanesulfonyl chloride, p-toluenesulfonyl chloride or benzenesulfonyl chloride.

4. The process of claim 3 wherein Ar is 6-methoxy-2-naphthyl and $R_1$ is methyl.

5. The process of claim 3 wherein Ar is 4-isobutylphenyl and $R_1$ is methyl.

6. The process of claim 3 wherein Ar is 3-phenoxyphenyl and $R_1$ is methyl.

7. A compound of the formula

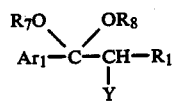

wherein $Ar_1$ is phenyl, phenoxyphenyl, naphthyl or biphenyl, optionally substituted with lower alkyl, lower alkoxy or halo, $R_1$, $R_7$ and $R_8$ are lower alkyl having 1–4 carbon atoms inclusive, and Y is an alkyl, cycloalkyl, alkenyl, alkynyl, aryl or aralkyl sulfonyloxy group.

8. The compound of claim 7 wherein $Ar_1$ is 6-methoxy-2-naphthyl.

9. The compound of claim 8 which is 1,1-dimethoxy-1-(6-methoxy-2-naphthyl)prop-2-yl methanesulfonate.

10. The compound of claim 8 which is 1,1-dimethoxy-1-(6-methoxy-2-naphthyl)prop-2-yl p-toluenesulfonate.

11. The compound of claim 8 which is 1,1-dimethoxy-1-(6-methoxy-2-naphthyl)prop-2-yl benzenesulfonate.

12. The compound of claim 7 wherein $Ar_1$ is 4-isobutylphenyl.

13. The compound of claim 12 which is 1-(4-isobutylphenyl)-1,1-dimethoxyprop-2-yl methanesulfonate.

14. The compound of claim 7 wherein $Ar_1$ is 1,1-dimethoxy-1-(3-phenoxyphenyl)propan-2-ol.

15. The compound of claim 14 which is 1,1-dimethoxy-1-(3-phenoxyphenyl)prop-2-yl methane-sulfonate.

16. A compound of the formula

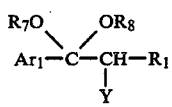

wherein $Ar_1$ is phenoxyphenyl, naphthyl or biphenyl, optionally substituted with lower alkyl, lower alkoxy or halo and $R_1$, $R_7$ and $R_8$ are lower alkyl having 1–4 carbon atoms inclusive.

17. The compound of claim 16 wherein $Ar_1$ is 6-methoxy-2-naphthyl.

18. The compound of claim 17 which is 1,1-dimethoxy-1-(6-methoxy-2-naphthyl)propan-2-ol.

19. The compound of claim 16 wherein $Ar_1$ is 3-phenoxyphenyl.

20. The compound of claim 19 which is 1,1-dimethoxy-1-(3-phenoxyphenyl)propan-2-ol.

21. The compound which is 1-(4-isobutylphenyl)-1,1-dimethoxypropan-2-ol.

* * * * *